United States Patent [19]

Muller

[11] 4,357,940

[45] Nov. 9, 1982

[54] TISSUE PNEUMATIC SEPARATOR STRUCTURE

[75] Inventor: George H. Muller, Ann Arbor, Mich.

[73] Assignee: Detroit Neurosurgical Foundation, Detroit, Mich.

[21] Appl. No.: 103,206

[22] Filed: Dec. 13, 1979

[51] Int. Cl.³ .............................................. A61B 17/00
[52] U.S. Cl. ............................ 128/303 R; 128/303.11
[58] Field of Search ............... 17/1 G, 21, 51; 433/80, 433/83, 86, 119, 120; 222/3, 5; 239/DIG. 21, DIG. 20, DIG. 22; 15/405, 316 R; 128/303 R, 303.11, 325

[56] References Cited

U.S. PATENT DOCUMENTS

| | | | |
|---|---|---|---|
| 3,117,726 | 1/1964 | Schöberg | 15/405 |
| 3,241,239 | 3/1966 | Ellis | 433/120 |
| 3,984,054 | 10/1976 | Frochaux | 239/DIG. 21 |
| 4,060,874 | 12/1977 | Farutsutsumi | 15/405 |
| 4,091,999 | 5/1978 | Voos | 239/DIG. 22 |
| 4,118,830 | 10/1978 | Weiland | 222/5 |
| 4,298,074 | 11/1981 | Mattchen | 128/303 R |

FOREIGN PATENT DOCUMENTS 974101  9/1975  Canada ................................. 433/86

OTHER PUBLICATIONS

"Flange", New Collegiate Dictionary, Merriam-Webster Co., Springfield, Mass.

Primary Examiner—Richard J. Apley
Assistant Examiner—J. L. Kruter
Attorney, Agent, or Firm—Whittemore, Hulbert & Belknap

[57] ABSTRACT

Structure for and a method of separating tissue pneumatically comprising a source of gas under pressure, a regulator for regulating the pressure of the gas, and flow controls for directing the pressure controlled gas to a disposable gas directing stem and head assembly, and the method of use of such structure comprising directing gas under controlled pressure and direction toward tissue to be separated.

28 Claims, 18 Drawing Figures

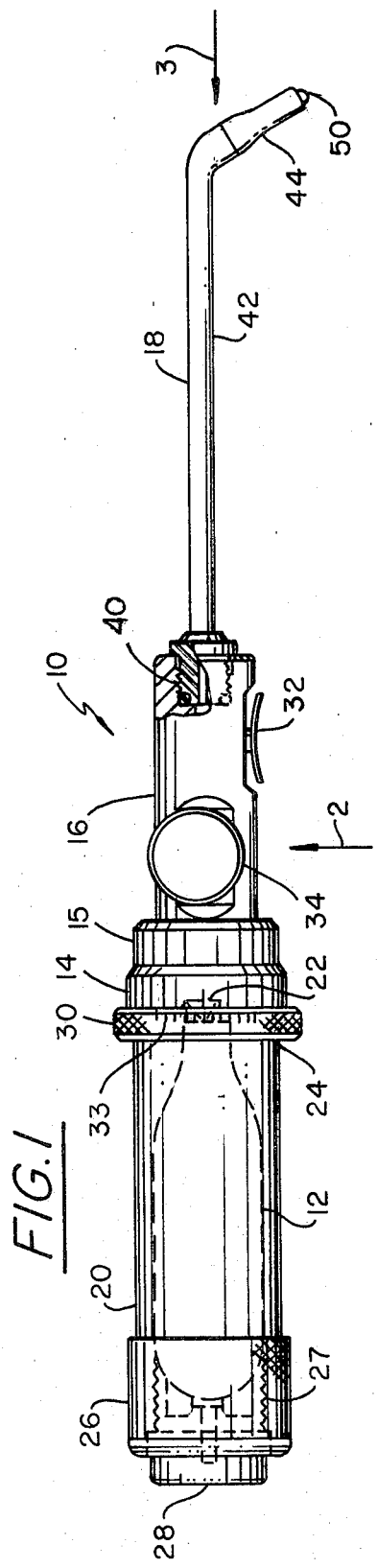
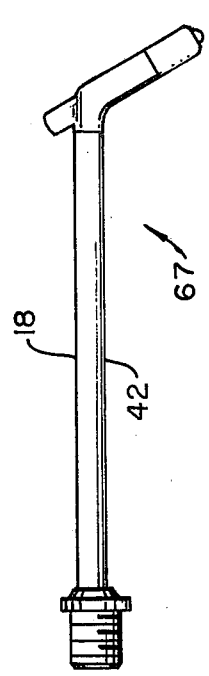
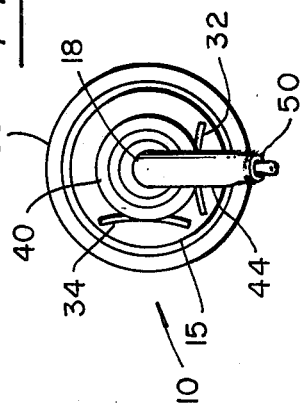
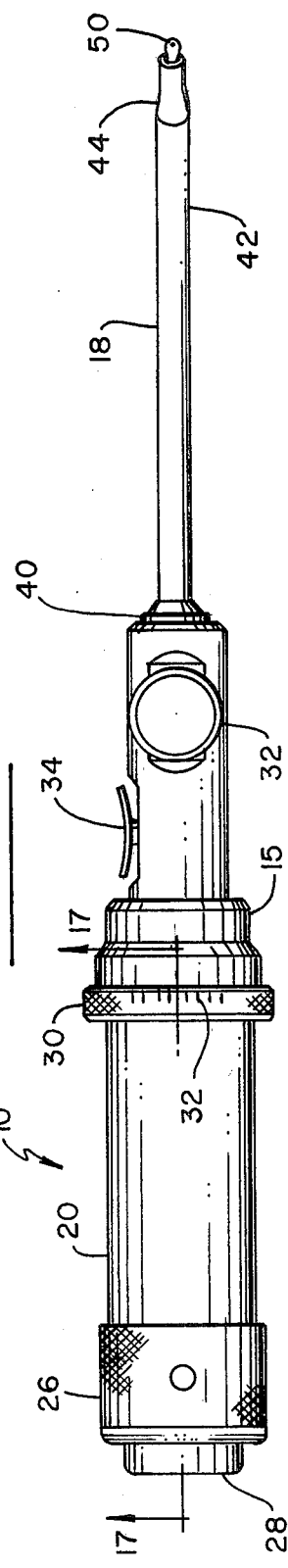

TISSUE PNEUMATIC SEPARATOR STRUCTURE

BACKGROUND OF THE INVENTION

1. Field of the Invention

The invention relates to tissue separators and refers more specifically to a tissue pneumatic separator device for directing a suitable gas under pressure toward tissue layers to be separated at a controlled head pressure through a calibrated orifice or jet of specified length and in a controlled direction, which is portable and autonomous and the method of using such a device to direct gas under controlled pressure and in a controlled direction through an orifice toward tissue to be separated.

2. Description of the Prior Art

In the past prior structure for separating tissue such as tumor sacs or membranes from surrounding healthy tissue has included primarily cutting and/or physical nudging apparatus, held in the hand of a surgeon, requiring actual contact with the tissue to be separated. Vibrating heads or physical nudging apparatus have also been used in the past. Devices such as scalpels have sometimes caused such undesired damage to and bleeding from tissue being separated. Ultrasonic vibrating heads often use cumbersome umbilical connections to nearby generally floor mounted generators with electrical power inputs and are very expensive. All such devices have of necessity required extreme care, patience and delicate manipulation in their use to minimize such damage.

SUMMARY OF THE INVENTION

In accordance with the invention, there is provided a tissue pneumatic separator device (of approximately the size of a felt pen) and a method which utilizes suitable gas at a controlled head pressure flowing through a calibrated orifice of specified diameters and length and in variously controlled direction to separate layers of tissue rapidly, accurately and without damage to both or at least one of the layers or membranes.

The device comprises a source of gas under pressure, means for regulating the gas pressure directed toward the tissue to be separated, controls for controlling the flow of gas to the tissue to be separated, and a disposable head and stem assembly for directing the regulated, controlled gas toward the tissue to be separated.

The method of the invention comprises directing gas under preselected pressure through on-off controls to a gas directing head and stem assembly containing the calibrated orifice or jet toward the tissue to be separated in a plurality of air patterns.

BRIEF DESCRIPTION OF THE DRAWINGS

FIG. 1 is a side elevation view of the tissue pneumatic separator structure of the invention for practicing the tissue pneumatic separation method of the invention.

FIG. 2 is a top view of the tissue pneumatic separator structure illustrated in FIG. 1, taken substantially in the direction of arrow 2 in FIG. 1.

FIG. 3 is an end view of the tissue pneumatic separator structure illustrated in FIGS. 1 and 2, taken in the direction of arrow 3 in FIG. 1.

FIG. 4 is a side elevation view of a modified disposable head and stem assembly for the tissue pneumatic separator structure of FIGS. 1-3.

DESCRIPTION OF THE PREFERRED EMBODIMENT

Figure 5:
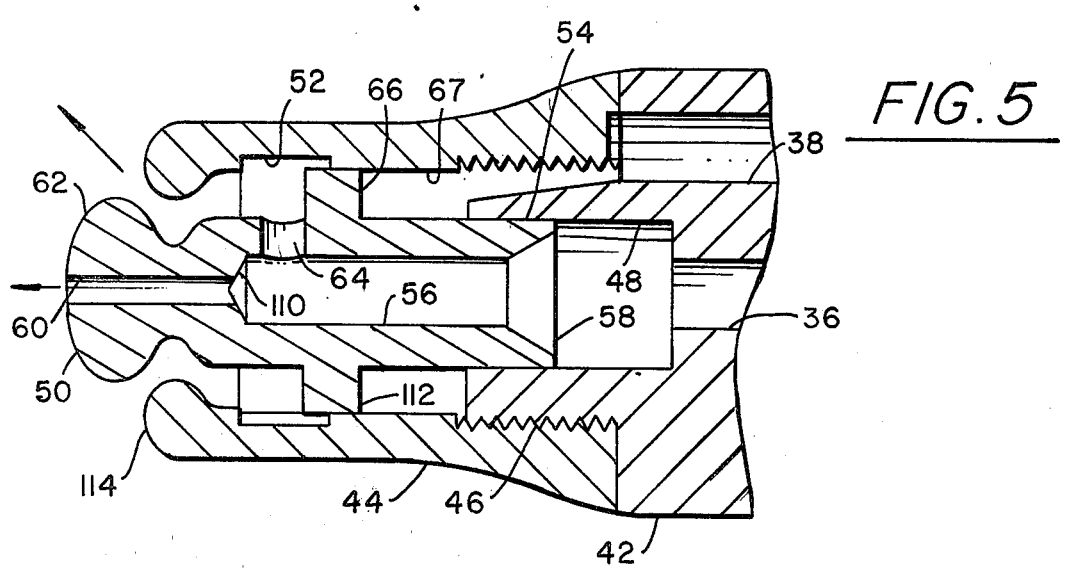
FIG. 5 is a partial longitudinal section view of the disposable head, stem assembly and related jet orifices of the tissue pneumatic separator structure of FIGS. 1-3 with the tip in one operating position thereof.

The tissue pneumatic separator 10 includes a source of gas under pressure 12, means for regulating the head pressure of the gas 14, on-off flow control means 16 for controlling feeding of the gas under regulated head pressure to the head and stem subassembly 18, and disposable head and stem structure 18.

The source of gas under pressure, as shown, is a medical carbon dioxide cartridge which may be purchased from Kidde Manufacturing Company as part No. 561207. The cartridge 12 may be filled with gas such as carbon dioxide or nitrogen, or other suitable gases which will not cause embolism or otherwise react unfavorably with open blood vessels and bleeding living tissue material.

When the cartridge 12 is filled with carbon dioxide, it may have between 8.5 and 9.1 grams of carbon dioxide therein and at room temperature of 70° it will be under pressure of 850 psi. At one atmosphere the carbon dioxide will have a volume of approximately 280 cu. in. The compressed volume of the carbon dioxide as a liquid within the cartridge may be 0.63 cu. in. Such cartridges may not be used above 150°.

At 2 cu. in. per second release, such cartridges provide 140 seconds or approximately two minutes of continued gas pressure operation at 2 psi.

The capsule 12 is placed in a cylindrical cartridge receiving chamber 20 having known cartridge piercing structure 22 in end 24 thereof. The cartridge 12 is caused to be punctured by the cartridge piercing structure 22 on securing of the cap 26 to the chamber 20. Cap 26 may be secured to the chamber 20 by convenient means such as threads 27. The end 28 of the cap 26 appears with a red ring 29 therearound to indicate the dangerously high pressure within the chamber 20 on piercing of the cartridge 12 once the cap 26 is screwed in and the cartridge 12 is pierced.

More specifically, the cartridge piercing structure 22 includes the cylindrical knife 23 secured to the partition 25 in the chamber 20. An annular resilient sealing member is positioned around the cylindrical knife for sealing capsule 12 before it is pierced by the knife 23.

Figure 17:
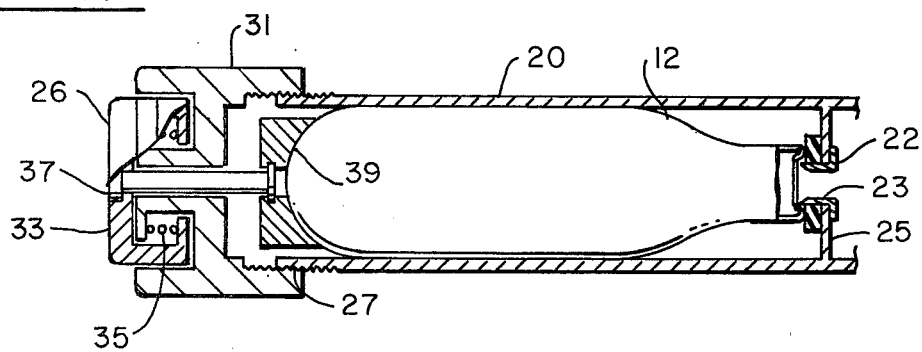
FIGS. 17 and 18 are longitudinal section views of a portion of the tissue pneumatic separator structure of FIG. 1, taken substantially on line 17—17 in FIG. 2, with the end cap in different positions indicating perforated and non-perforated pressure capsules respectively.
Figure 18:
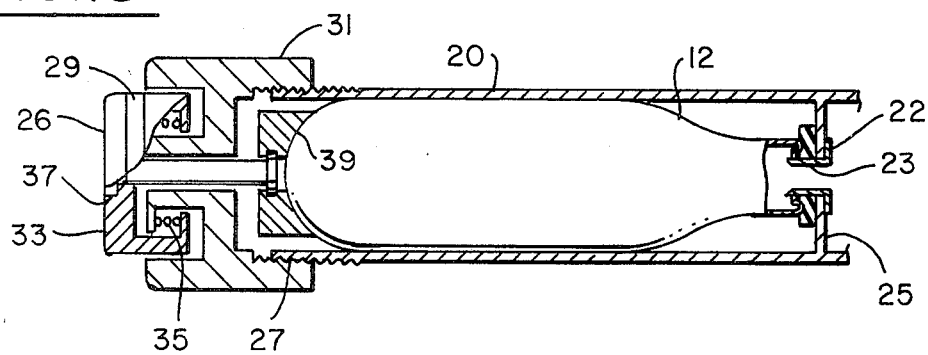

The cap 26 includes the outer generally cylindrical member 31 having the axial cross sectional shape illustrated in FIGS. 17 and 18, the end member 33 again having the axial cross sectional shape as shown in FIGS. 17 and 18 and the coil spring 35 bearing the members 31 and 33 as shown. Cap 26 further includes the axially extending rivet member or stud 37 which is rigidly secured to the end member 33 at one end thereof and which is rotatably secured to the capsule abutment 39 at the other end thereof. The capsule abutment member 39 has the axial cross sectional shape, again as shown in FIGS. 17 and 18.

The red ring 29 is provided on the end member 33 of the cap 26 in the position shown in FIGS. 17 and 18, whereby when the end cap 26 is screwed onto the chamber 20 sufficiently to pierce the capsule 12, the red ring will be exposed to indicate high pressure within the chamber 20 and the unadvisability of autoclave procedure.

In operation, after a capsule 12 is placed in chamber 20 as shown in FIG. 17 and the member 31 is threaded onto the chamber 20, the threading onto the chamber 20 of the member 31 of cap 26 causes the spring 35 to compress and the member 33 to be pulled toward the chamber 20. The member 33 through the rivet 37 and the abutment 39 provides pressure on the capsule 12 which will cause it to be pierced by the knife 23.

The means 14 for regulating the pressure of the gas is a two-stage control which first causes the gas in the cartridge 12 to be emptied into the chamber 15 at between 20–50 psi. This pressure is not adjustable. The knurled wheel 30 is a pressure adjustment and adjusts the 20–50 psi in chamber 15 to 2 to 12 psi range output of controlled gas release into flow control section 16. Gas at a pressure of 2 to 12 psi is caused to be released into the flow control valves of section 16.

The flow control section 16 includes a forefinger plunger type control 32 and a thumb plunger type control 34. The plunger type controls 32 and 34 are on-off valves and permit pressure to flow into the head and stem assembly 18 in the passage 36 and 38 respectively at the regulated 2 to 12 psi head pressure range as sensed at the head or outer end of the stem. The plunger type flow control member 32 and 34 may be activated to determine the direction of gas flow from the head and stem assembly 18 in accordance with the tip utilized therewith as will be seen subsequently. Plunger type flow control valves such as 32 and 34 are readily available, and are within the skill of the art to readily produce and will not, therefore, be considered in detail herein. It should, however, be noted that they are preferably interconnected so that when one is open the other is closed.

The head and stem assembly 18 is secured to the flow control section 16 of the tissue pneumatic separator 10 by quick disconnect structure 40 and is intended to be optionally disposable. Quick disconnect structures 40 are readily available. Typically, they may include an indexed threaded connection and an annular groove carrying an O-ring seal. The indexed threads insure proper angular positioning of the head and stem assembly 18 on the tissue pneumatic separator. The details thereof will not therefore be considered further herein.

Head and stem assembly 18 includes the stem portion 42 which provides passages 36 and 38 to the removable head portion 44 of the tissue pneumatic separatoer 10, as shown best in FIG. 5.

As shown in FIG. 5, the head portion 44 is removably secured to the stem portion 42 and is secured thereto by convenient means such as the interference threads 46.

If stem portion 42 is constructed of stainless steel or aluminum, the head portion 44 could be injected plastic to provide sufficient interference to prevent gas breakage at interface 43 without the need for an O-ring and groove seal.

Figure 6:
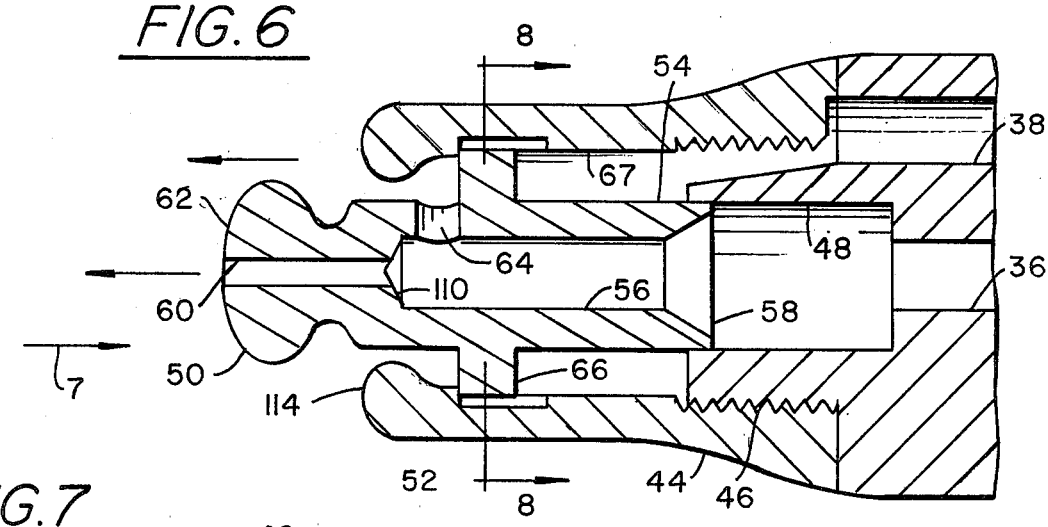
FIG. 6 is a partial longitudinal section view of the disposable head and stem assembly of the tissue pneumatic separator structure of FIGS. 1-3 with the tip in another operating position thereof.
Figure 7:
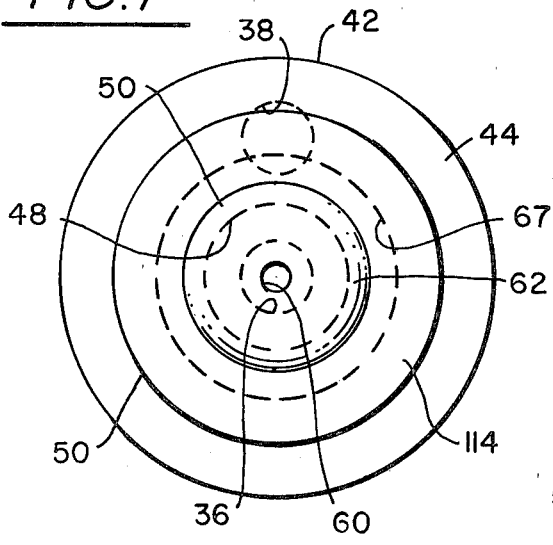
FIG. 7 is an end view of the head structure illustrated in FIG. 6, taken substantially in the direction of arrow 7 in FIG. 6.
Figure 8:
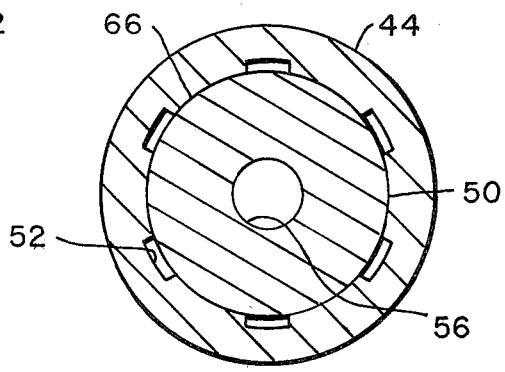
FIG. 8 is a cross section of the head structure illustrated in FIG. 6, taken substantially on the line 8—8 in FIG. 6.

The stem portion 18 further includes the recess 48 therein as shown best in FIGS. 5 and 6 for receiving the tip 50 of the head and stem assembly of the tissue pneumatic separator 10.

The head 44 of the head and stem assembly 18 as shown is cylindrical and has a plurality of angularly spaced apart longitudinally extending slots 52 on the inner bearing surface thereof. The tip 50 is constructed to slide axially within the head 44.

The tip 50 as shown in FIGS. 5 and 6 is also a cylindrical member since it interfaces with cylindrical portions of the chamber 67 of the head 44. Tip 50 has a shank 54 which is received for axial reciprocation in the recess 48 in the stem portion 42 of the head and stem assembly 18. The inner cylindrical surface acts as a bearing for shank 54 of tip 50.

The tip 50 further includes a larger diameter, axially extending opening 56 in end 58 thereof which in stem 50 is coaxial with the smaller diameter calibrated orifice or jet 60 extending through the outer end 62 thereof, again, as shown best in FIGS. 5 and 6. A transversely extending passage 64 communicates with the inner end of the axially extending opening 56 in the tip 50.

Tip 50 further includes the annual outer piston like flange 66. The piston like flange 66 and the shank 54 of the tip 50, together with the recess 48, guide the tip 50 in axial movement relative to the stem 42 and head 44 of the head and stem assembly 18 in operation of the tissue pneumatic separator 10.

Figure 9:
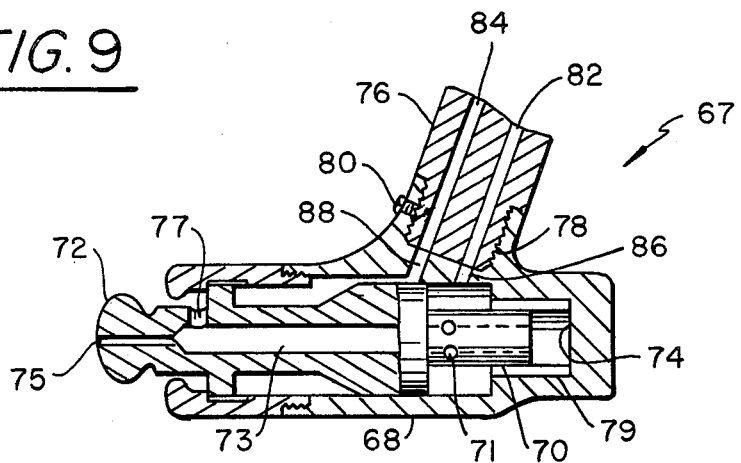
FIG. 9 is an enlarged partial longitudinal section view of the head and stem assembly of the modified replaceable head and stem assembly illustrated in FIG. 4 which includes an additional posterior guidance and bearing extension.

In the modified head and stem assembly 67 illustrated in FIG. 9, the shank 70 of the tip 72 is provided with radial openings 71 therethrough in communication with axial openings 73 and 75 and radial opening 77 in tip 72 and is elongated and extends into a bearing sleeve 79 in recess 74 in the head 68 to improve guiding of tip 72 in movement in the head 68. The head 68 is secured to the modified stem 76 by convenient means such as a threaded fit 78 and aligning means 80 which provide alignment between openings 82 and 84 in the stem 76 with the openings 86 and 88 in the head 68. These openings are similar to the openings 38 and 36 in the head and stem structure of FIGS. 5 and 6 and deliver pressure regulated flow controlled gas to the head 68 and tip 72 substantially in the same manner as the gas is delivered to the head 44 and tip 50 of the head and stem assembly 18 of the tissue pneumatic separator of FIG. 10.

The modified tip structure of FIGS. 10-15 may be used with either the head and stem assembly 18 or with modified head and stem assembly 67 as shown in FIG. 9.

Figure 10:
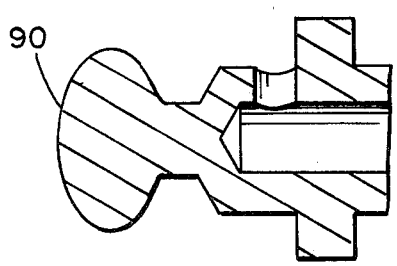
FIG. 10 is a partial longitudinal section view of modified tip structure for use in the tissue pneumatic separator of FIGS. 1-3 that includes a bulbous tip without a calibrated axial orifice.

The modified tip 90 shown in FIG. 10 is the same as the tip 50 illustrated in FIGS. 5 and 6 with the single exception that the axial calibrated orifice or jet 60 is not provided therein.

The modified tip 92 of FIG. 11 is again exactly the same as the tip 50 with the single exception that the length of the tip through which the smaller diameter bore 94 extends is considerably longer than the portion of the tip 50 through which the smaller diameter calibrated orifice 60 extends.

Figure 11:
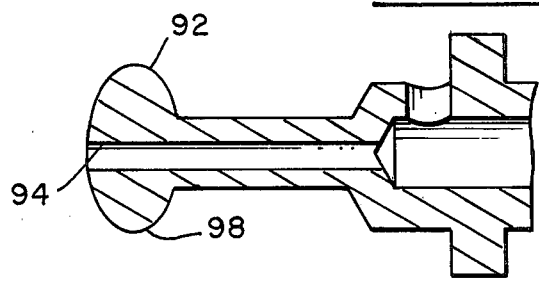
FIG. 11 is a partial longitudinal section view of another modified tip for use with the tissue pneumatic separator structure of FIGS. 1-3 that includes an extended working bulbous tip with a calibrated axial orifice.
Figure 12:
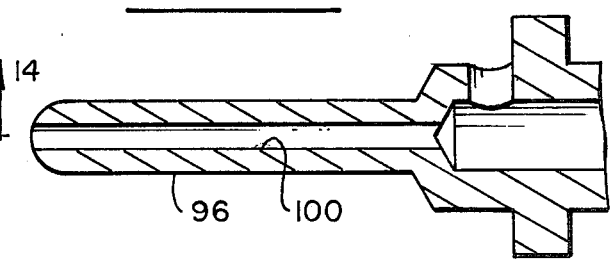
FIG. 12 is a partial longitudinal section view of another modified tip for use with the tissue pneumatic separator structure of FIGS. 1-3 that includes an extended working tip without a bulbous anterior extremity, and a calibrated axial orifice.

The tip 96 of FIG. 12 is similar to the tip 92 of FIG. 11 with the exception that the bulbous end 98 of the tip 92 is missing and the tip 96 is again further elongated in the area in which the smaller diameter opening 100 extends.

Figure 13:
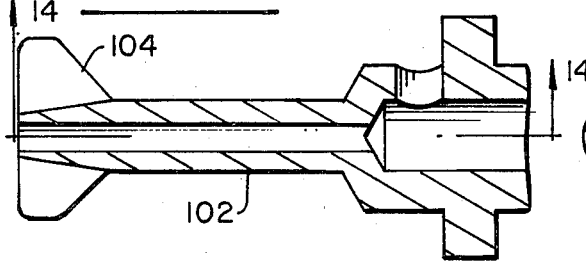
FIG. 13 is a partial longitudinal section view of another modified tip for use with the tissue pneumatic separator structure of FIGS. 1-3 which is similar to the top of FIG. 12, but includes a spatula-like anterior extremity.
Figure 15:
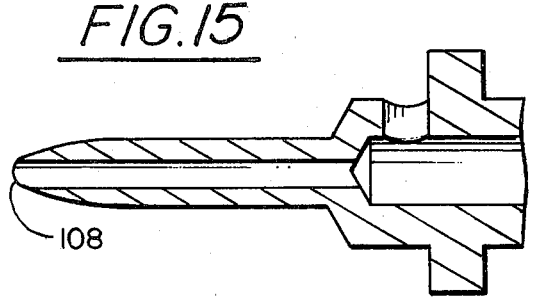
FIG. 15 is a partial longitudinal section view similar to that of FIG. 14 of modified tip structure such as shown in FIG. 13 wherein the anterior extremity is blunter.
Figure 14:
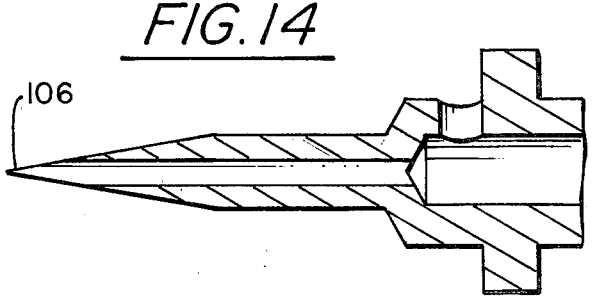
FIG. 14 is a partial longitudinal section view of the tip structure illustrated in FIG. 13, taken substantially in the direction of arrow 14 in FIG. 13.

The tip 102 illustrated in FIG. 13 is similar to the tip 96 illustrated in FIG. 12 but has a wider, flat, spatula like blund end 104 thereon. The spatula like tip 104 of the tip of FIG. 13 is further modified by having a relatively sharper outer end 106 as shown in FIG. 14, and relatively flunt or rounded outer end 108 as shown in FIG. 15.

Any of the tips 92, 96 and 102 may be provided without the smaller diameter calibrated orifice therethrough. Such modification of these tips and their use would depend upon the type of tissue to be separated and the desired gas pattern from the tissue pneumatic separator 10.

The tips 90, 92, 96 and 102 in both of its modifications are interchangeable with the tip 50, and the tip 72 as shown in FIGS. 5, 6 and 9 respectively and are used in accordance with the nature of the tissue to be separated and the related necessary tissue separation precautions and procedures.

In use of the tissue pneumatic separator 10, the cartridge 12 is first inserted into the chamber 20 to provide a controlled but unregulated pressure of from 20 to 50 psi within the chamber 20. The pressure regulator 14 is then set to the desired source pressure of between 2 to 12 psi output by rotation of the pressure regulating member 30 into alignment at the correct position on the scale 33 thereof. At this point, the regulated desired gas pressure is available at the flow control section 16 and the red tip 28 of the cap 26 indicates the loaded condition of the tissue pneumatic separator 10.

The head 44 of the tissue pneumatic separator 10 is then positioned adjacent to the tissue it is desired to separate and the forefinger control 32 and the thumb control 34 are manipulated alternatively and/or each intermittently as desired to provide the required pattern of gas flow at the regulated pressure. The gas in turn then impinges on the tissue to be separated to provide the desired tissue separation.

Referring particularly to FIG. 5 and in more detail, with the forefinger flow control valve open, that is, with the valve 32 depressed, gas under the required head pressure is passed through the stem 42 in the passage 36 and enters the chamber 48 and the passage 56 and exits the tip 50 through the calibrated axial orifice 60. At this time the tip 50 is forward due to the impingement of the gas on the annular areas 58 and 110. The resulting gas flow from the smaller diameter calibrated orifice 60 is in a very small circular pattern or jet of gas travelling at a relatively high velocity. In other words, a very focused gas stream is provided substantially only through the orifice 60. The position of the stem 50 at this time is substantially as shown in FIG. 6. It is in its extreme forward position.

With the forefinger control valve closed, if the thumb control valve is depressed, regulated gas under the controlled head pressure is passed through the passage 38 and impinges on the inner annular surface 112 of the piston like 66 to push the flange 66 forward to the point where the flange 66 is diametrically opposite the slots 52. Since the slots 52 are longer than the axial dimension of the flange 66, the gas pressure will neutralize on both sides of flange 66 with the flange 66 located substantially centrally of the slots 52 and gas will escape through the annular opening or large orifice between the partly extended bulbous tip 50 and the controlled cross-section end 114 of the head 44. Such operation will provide a continuous cylindrical wall shaped gas stream which will tend to disperse radially as it leaves the head 44 and tip 50 depending on the contour, curvature and general shape of end 114. Such gas configuration provides less local unit pressure and velocity and may be used for clean-up after tissue separation whereas the very sharply focused gas stream obtainable with the pressure of the forefinger control only may be used on a small target primarily for separation.

When the blind tips such as 90 are used, that is, tips without the smaller diameter, axial opening 60 therethrough, on depression of the forefinger flow control valve, the tip will again be moved forward. However, the gas will flow out through the passage 64 and will again provide a cylindrical gas pattern flow between the contoured cross section end 114 and the bulbous head which will be directed substantially axially from the head in view of the greater separation between the end 114 of the head 44 and the tip 50 provided, as indicated in FIG. 6 wherein the tip 50 is at its extreme outer position.

With the blind tip such as 90, when the gas is permitted to flow in the passage 38, the tip 90 again moves to a position substantially centrally of the slots 52 to provide the cylindrical wall shaped flow of gas between the tip 90 and the head 44 which disperses radially in view of the rather close proximity of the tip and the end 114 of the head 44.

The overall operation of the tissue pneumatic separator 10 with the modified head and stem assembly 67 secured thereto is substantially the same as that indicated above. As indicated previously, the head and tip 67 provides a greater stability for the axial reciprocation of the tip 72 to avoid jamming the piston and may, therefore, be preferable in some instances.

The different tip configurations illustrated in FIGS. 11, 12 and 13 and the modifications of the tip configuration shown in FIGS. 14 and 15 are useful under certain circumstances where, for example, it is desired to extend the bulbous end 98 of a tip 92 substantially beyond the tip 14 of the head 44 to either further control the particular pattern of escaping gas or increase the visibility for the surgeon near the operating end of the tip. The tips of FIGS. 11 and 12 are particularly advantageous in working, for example, in restricted areas and where physical pressure and/or nudging operating together with the pneumatic separation of the tissue due to the impingement of the gases thereon is desired.

While the tissue pneumatic separator of the invention has been considered in conjunction with the separator of a tumor sac from surrounding tissue such as brain tissue, it will be understood that the use of the tissue pneumatic separator of the invention is not so restricted. Thus, it is emphasized that larger and smaller modifications of the invention and with different pressure may be utilized to perform other tissue separating requirements such as less delicate operations, autopsies, and tissue separation in removing glands from animals for scientific and pharmaceutical uses and even in the butchering of significantly larger animals and the like.

The tissue pneumatic separator thus disclosed has tactile feedback, as obtained by the working tip when subjected to tissue resistance on one side and operating pressure on the other, as the surgeon moves the whole assembly back and forth. This may be needed to help differentiate between tissue structures and will separate a broad range of tissue precisely without pulling and tugging on surrounding tissue without the use of sharp cutting edges. At the same time the tissue pneumatic separator 10 gives the surgeon complete autonomy in that the separator is held and controlled solely by the surgeon without umbilical connections to a gas or power source.

Figure 16:
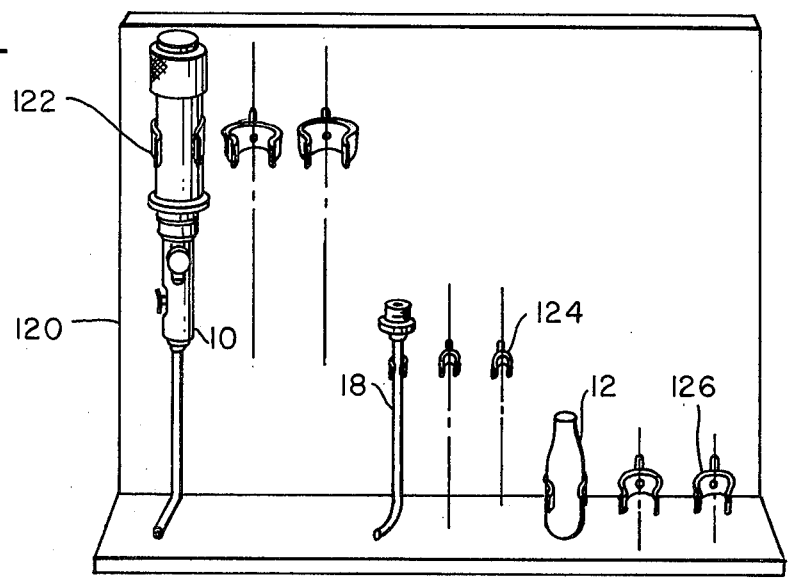
FIG. 16 is a perspective view of a rack for use with a plurality of the tissue pneumatic separators or parts thereof.

Further, as shown in FIG. 16, a rack 120 having spring clips 122, 124 and 126 thereon for holding spare tissue pneumatic separator 10, disposable head and stem assemblies 18 and gas cartridges 12, respectively, may be provided to facilitate the use of the tissue pneumatic separators 10, if desired. The rack 120 may be constructed to hold a number of only one article, if desired.

While one embodiment of the present invention has been considered in detail, along with several species and modifications thereof, it will be understood that other embodiments and modifications are contemplated. For example, where desired, the source of gas under pressure may be located at a distance from the flow control and head and stem assembly and be connected thereto with an umbilical pressure hose for extended operations without running out of gas. Also, the specific structure disclosed prior to the head and stem assembly 18 is not essential. Thus, any means of providing the required air pressure to the passages 36 and 38 at the selection of the surgeon will provide effective operation of the head and stem assembly in accordance with the invention. Further, in a less complicated tissue pneumatic separator, a single flow control valve may be utilized. All such embodiments and modifications of the disclosed invention are intended to be included within the scope of the invention as are defined by the appended claims.

I claim:

1. A tissue pneumatic separator comprising a source of a compressed gas under pressure, means connected to the source of gas for directing gas therefrom at tissue to be separated, including a pneumatic activated floating tip adapted to be applied to body tissue at a wound site, positioned on the tissue pneumatic separator through which the gas is directed at the tissue the position of which tip is determined by the pressure of the gas and external mechanical force applied thereto in opposition to the gas pressure.

2. Structure as set forth in claim 1, wherein the means for directing the gas at tissue to be separated further includes an elongated cylindrical stem and a cylindrical head secured to the stem in which the tip floats for securing the tip to the stem.

3. Structure as set forth in claim 2, wherein the floating tip has an axial passage therethrough whereby the gas under pressure is allowed to exit the floating tip centrally thereof and the floating tip also has a radially extending passage therein through which the gas under pressure is permitted to excape from the floating tip and pass radially between the tip and head.

4. Structure as set forth in claim 2, wherein the tip and head are positioned at an angle to the longitudinally extending axis of the stem.

5. Structure as set forth in claim 1, wherein the floating tip has an axial passage therethrough whereby the gas under pressure is allowed to exit the floating tip centrally thereof.

6. Structure as set forth in claim 1, wherein the floating tip has a radially extending passage therein through which the gas under pressure is permitted to escape radially from the floating tip.

7. Structure as set forth in claim 6 and further including a radially extending piston like flange on the floating tip centrally thereof positioned axially inwardly of the tissue pneumatic separation relative to the radially extending passage.

8. A tissue pneumatic separator comprising a cylindrical elongated stem having a central axially extending passage therethrough and a radially outer axially extending passage therethrough extending substantially parallel to the central passage, a source of gas under pressure secured to one end of the stem for providing gas under pressure through the central and radially outer passage, separate manually operated valve means for regulating the gas pressure through both passages a cylindrical head secured to the other end of the stem including a smaller axially outer diameter and an angularly spaced-apart longitudinally extending slots in the radially inner surface of the head adjacent to the outer end thereof, an axially extending recess in said other end of the stem and a floating tip positioned within the head defining an annular space therebetween, one end of which is positioned within the recess in the stem for guided reciprocal movement therein, which tip has a radially extending piston like flange thereon centrally thereof in engagement with the radially inner surface of the head centrally thereof for guiding reciprocal movement of the tip within the head, the head and floating tip providing an escape passage therebetween for gas in the radially outer passage between the other end of the head and the tip, said tip having an axially extending central passage therethrough for permitting excape of air through the central passage of the stem and a radially extending passage in said tip connecting to the central axially extending passage in the tip for permitting gas to escape through the annular space between the tip and head.

9. Structure as set forth in claim 8, wherein the head and tip are positioned at an angle to the longitudinal axis of the tissue pneumatic separator.

10. A tissue pneumatic separator comprising a source of compressed gas under pressure, means connected to the source of gas under pressure for directing gas therefrom at tissue to be separated, including a stem one end of which is connected to the source of gas under pressure having a central axially extending passage therethrough and a second axially extending passage therethrough parallel to the central axially extending passage, and a head and tip secured to the other end of the stem connected to the stem to permit gas from the central passage to escape through the stem and between the stem and head and to permit gas from the second passage through the stem to escape between the head and the stem.

11. Structure as set forth in claim 10, wherein the tissue pneumatic separator further includes a forefinger actuated valve for controlling the flow of gas under pressure through the central axial passage through the stem.

12. Structure as set forth in claim 10, wherein the tissue pneumatic separator further includes a thumb actuated valve for controlling the flow of gas under pressure through the radially outer axial passage through the stem.

13. A tissue pneumatic separator comprising a source of gas under pressure, floating tip means connected to the source of gas for directing gas therefrom at tissue to be separated including an elongated cylindrical stem and a cylindrical head secured to the stem in which the tip floats for securing the top to the stem, and a floating tip adapted to be applied to body tissue at a wound site, positioned on the tissue pneumatic separator through which the gas is directed at the tissue, the position of which tip is determined by the pressure of the gas and external mechanical force applied thereto in opposition to the gas pressure, said stem having a central axially extending longitudinal passage therethrough and a second longitudinally extending passage therethrough substantially parallel with the central axially extending passage, which passages are in communication with the tip and with a space defined between the tip and head respectively.

14. Structure as set forth in claim 13, wherein the tissue pneumatic separator further includes a forefinger actuated valve for controlling the flow of gas under pressure through the central passage.

15. Structure as set forth in claim 13, wherein the tissue pneumatic separator further includes a thumb actuated valve for controlling the flow of gas under pressure through the second passage through the stem and around the floating tip.

16. Structure as set forth in claim 13, wherein the tip is provided with a radially extending flange forming a piston longitudinally centrally thereof in engagement with the radially inner surface of the head for guiding the tip in axially reciprocal movement within the head and the head is provided with angularly spaced apart axially extending slots on the radially inner surface thereof for permitting by-pass of gas under pressue around the flange with the flange in pre-determined axial positins relative to the head.

17. Structure as set forth in claim 16, wherein the radially extending passage is positioned in front of the piston on the tip.

18. Structure as set forth in claim 13, wherein the floating tip has an axial passage therethrough whereby the gas under pressure is allowed to exit the floating tip centrally thereof.

19. Structure as set forth in claim 13, wherein the floating tip has a radially extending passage therein through which the gas under pressure is permitted to escape radially from the floating tip.

20. Structure as set forth in claim 13 and further including a radially extending piston like flange on the floating tip centrally thereof positioned axially inwardly of the tissue pneumatic separation relative to the radially extending passage.

21. Structure as set forth in claim 13, wherein the floating tip has an axial passage therethrough whereby the gas under pressure is allowed to exit the floating tip centrally thereof and the floating tip also has a radially extending passage therein through which the gas under pressure is permitted to escape from the floating tip and pass radially between the tip and head.

22. Structure as set forth in claim 13, wherein the tip and head are positioned at an angle to the longitudinally extending axis of the stem.

23. A tissue pneumatic separator comprising a source of compressed gas under pressure, floating tip means connected to the source of gas for directing gas therefrom at tissue to be separated, includes an elongated cylindrical stem and a cylindrical head secured to the stem in which the tip floats for securing the tip to the stem and a floating tip adapted to be applied to body tissue at a wound site, positioned on the tissue pneumatic separator through which the gas is directed at the tissue, the position of which tip is determined by the pressure of the gas and external mechanical force applied thereto in opposition to the gas pressure, said stem including a recess provided in the end of the stem for receiving one end of the floating tip for guiding the tip in axially reciprocal movement relative to the stem and head.

24. Structure as set forth in claim 23, wherein the floating tip has an axial passage therethrough whereby the gas under pressure is allowed to exit the floating tip centrally thereof.

25. Structure as set forth in claim 23, wherein the floating tip has a radially extending passage therein through which the gas under pressure is permitted to escape radially from the floating tip.

26. Structure as set forth in claim 23 and further including a radially extending piston like flange on the floating tip centrally thereof positioned axially inwardly of the tissue pneumatic separation relative to the radially extending passage.

27. Structure as set forth in claim 23, wherein the floating tip has an axial passage therethrough whereby the gas under pressure is allowed to exit the floating tip centrally thereof and the floating tip also has a radially extending passage therein through which the gas under pressure is permitted to escape from the floating tip and pass radially between the tip and head.

28. Structure as set forth in claim 23, wherein the tip and head are positioned at an angle to the longitudinally extending axis of the stem.

* * * * *